United States Patent [19]

Lehrer et al.

[11] Patent Number: 4,705,777

[45] Date of Patent: * Nov. 10, 1987

[54] CATIONIC OLIGOPEPTIDES HAVING MICROBICIDAL ACTIVITY

[75] Inventors: Robert I. Lehrer, Santa Monica; Michael E. Selsted; Tomas Ganz, both of Los Angeles, all of Calif.

[73] Assignee: The Regents of the University of California, Berkeley, Calif.

[*] Notice: The portion of the term of this patent subsequent to Sep. 24, 2002 has been disclaimed.

[21] Appl. No.: 750,378

[22] Filed: Jun. 28, 1985

Related U.S. Application Data

[63] Continuation-in-part of Ser. No. 705,455, Feb. 25, 1985, abandoned, which is a continuation-in-part of Ser. No. 609,410, May 11, 1984, Pat. No. 4,659,692, which is a continuation-in-part of Ser. No. 443,087, Nov. 19, 1982, Pat. No. 4,543,252, which is a continuation-in-part of Ser. No. 341,394, Jan. 21, 1982, abandoned.

[51] Int. Cl.⁴ .................. A61K 37/02; C07K 7/10

[52] U.S. Cl. ........................... 514/12; 530/324

[58] Field of Search .................. 530/324; 514/12

[56] References Cited

U.S. PATENT DOCUMENTS 4,543,252  9/1985  Lehrer et al. .................. 530/324

OTHER PUBLICATIONS

The Journal of Biological Chem., 258, (1983), 14485–14489.

Primary Examiner—Delbert R. Phillips
Attorney, Agent, or Firm—Bertram I. Rowland

[57] ABSTRACT

Novel microbicidal compositions are provided which find use as preservatives, disinfectants, antigens and the like. Particularly, cationic oligopeptides of up to about thirty-five amino acids are provided having amino acid sequences substantially comparable to the amino acid sequences of cationic oligopeptides produced by macrophage. A conserved framework structure is provided.

11 Claims, 1 Drawing Figure

FIG. 1

CATIONIC OLIGOPEPTIDES HAVING MICROBICIDAL ACTIVITY

CROSS-REFERENCE TO RELATED APPLICATIONS

This is a continuation-in-part of application Ser. No. 705,455, filed Feb. 25, 1985, now abandoned, which is a continuation-in-part of application Ser. No. 609,410, filed May 11, 1984, now U.S. Pat. No. 4,659,692, issued Apr. 21, 1987, which is a continuation-in-part of application Ser. No. 443,087, filed Nov. 19, 1982, now U.S. Pat. No. 4,543,252, issued Sept. 24, 1985, which is a continuation-in-part of application Ser. No. 341,394, filed Jan. 21, 1982, now abandoned, which disclosure are incorporated herein by reference.

BACKGROUND OF THE INVENTION

1. Field of the Invention

There is a continued interest in the development of novel microbicides which do not have adverse effects on the host, but have high potency against an undesirable pathogen or other microorganism. One area of interest in locating compounds which are microbicidally active are naturally occurring compounds which a host uses in its natural defense.

The function of macrophages and granulocytes, e.g., neutrophils, in host defense is well documented. There are numerous reports describing the cellular antimicrobial efficiency. See, for example, Hocking and Golde, *N. Engl. J. Med.* (1979) 301:580–587, who describe the role of rabbit alveolar macrophages, and Lehrer, *J. Clin. Invest.* (1972) 51:2566–2572 and Mandell, *Infect. Immun.* (1974) 9:337–341, who describe the antimicrobial activity of human neutrophils and human polymorphonuclear neutrophils.

Studies of the effect of granule extracts on microorganisms may be found in Rest et al., *Infect. Immun.* (1978) 19:131–137; Rest et al., ibid (1977) 16:145–151 and Modrzakowski et al., ibid (1979) 23:589–591. See also, Modrzakowski and Spitznagel, ibid (1979) 25:597–602, and Shafer et al., ibid (1984) 43:834–838, who report cationic proteins of greater than 30 kDal isolated from granules having bactericidal activity. As macrophages and granulocytes are thought to arise from a common stem cell and as these cells contain certain constituents in common (e.g. lysozyme), macrophages and neutrophils appear to be a potential source of compounds having microbicidal activity.

In order for naturally occurring compositions to be useful, there are many criteria. If one is to synthesize an oligopeptide, it is desirable that the number of amino acid units be relatively small. While hybrid DNA technology offers an opportunity to make large proteins, where a microbicidal protein is of interest, the toxic effect of the product on the host evidently creates difficulties in its economic synthesis. Secondly, the microbicidal compound should be independently active and not require the presence of a number of other materials for its activity. Where only a mixture of materials have the microbicidal activity, formulation problems can become severe. Thirdly, one is concerned with the environment in which the naturally occurring compound is active, that is, whether the naturally occurring compound can be formulated in such a way as to be acceptable to the host to be protected from the invading microorganism. Furthermore, by determining the amino acid composition and specific sequence, the peptide may be varied to enhance such properties as stability to degradation, biocidal activity, spectrum activity, and the like. Compounds having biocidal activity against a wide variety of microorganism are particularly important where there is no adverse effect on the host.

2. Description of the Prior Art

Zeya and Spitznagel, *J. Bacteriology* (1966) 91:755–762 describe cationic proteins of polymorphonuclear leukocyte lysosomes from guinea pigs. Zeya and Spitznagel, *Science* (1966) 154:1049–1051, describe the antimicrobial specificity of leukocyte lysosomal cationic proteins. Zeya and Spitznagel, *J. of Exp. Med.* (1968) 127:927–941, describe arginine-rich proteins of polymorphonuclear leukocyte lysosomes from rabbits. Patterson-Delafield et al., *Infection and Immunity* (1980) 30:180–192, report the isolation in impure form of microbicidal cationic proteins from rabbit alveolar macrophages. Patterson-Delafield et al., *Infection and Immunity* (1981) 31:723–731 (published Jan. 23, 1981) reports amino acid composition and functional attributes of impure microbicidal cationic proteins from rabbit alveolar macrophages. See also the references cited therein. Selsted et al., *J. of Biol. Chem.* (1983) 258:14485–14489, describe MCP-1 and MCP-2. See also, Lehrer et al., *Infection and Immunity* (1983) 42:10–14.

SUMMARY OF THE INVENTION

Novel antimicrobial oligopeptides are provided, having sequences comparable to cationic oligopeptides found in leukocytes. Particularly, the antimicrobial compounds have high cysteine and basic amino acid content, particularly arginine and share a common framework structure over a wide range of mammalian species.

DESCRIPTION OF THE SPECIFIC EMBODIMENTS

Microbicidal cationic proteins are provided having high cysteine and arginine content and consisting of cationic proteins derived from macrophages and granulocytes, fragments containing antimicrobial activity, and modified oligopeptides, having one or more amino acids substituted by a different amino acid from that found in the macrophages and granulocytes. The naturally occurring oligopeptides are characterized by having six cysteines and from two to four arginines, which are substantially conserved. The cysteines and arginines are dispersed throughout the oligopeptide, so that the cysteines provide for the opportunity for extensive crosslinking, intramolecularly and intermolecularly, covalently and non-covalently, and the arginines provide for positive charges throughout the molecule at a wide range of pHs, so as to be highly cationic. The subject compounds may be readily attached to a wide variety of other compounds, both poly(amino acids) and non-proteinaceous compounds, through one or more sulfur linkages or peptide linkages.

While the cysteine framework structure is preserved, as well as the excess of basic amino acids, (particularly arginine) over acidic amino acids, there appears to be substantial differences as to the intervening oligopeptides, depending on the source.

Non-primate oligopeptides, particularly rabbit, tend to be aliphatic, generally having not more than five amino acids having rings, particularly having not more than two aromatic amino acids and not more than two azole rings.

Primate oligopeptides, particularly human, tend to be more aromatic than non-primate, generally having at least four aromatic amino acids, where at least 40 number percent, particularly at least 50 number percent, are tyrosine.

For the most part, the compounds of this invention will have molecular weights in the range of about 3000–4000, usually 3100–3900 daltons, more usually for non-primates 3600–3900 daltons, and for primates 3100–3500 daltons. The subject compounds will show antimicrobial activity against a wide range of organisms, including viruses, bacteria and fungi.

The framework polypeptide will for the most part have the following formula:

$Z_{0-2}$—$(aa^1)_a$—$(aa^2)_b$—cys—$aa^4$—cys—arg—$aa^7$—$aa^8$—$aa^9$—cys—
—$aa^{11}$—$aa^{12}$—$aa^{13}$—glu—arg—$aa^{16}$—$aa^{17}$—gly—$aa^{19}$—cys—
—$aa^{21}$—$aa^{22}$—$aa^{23}$—gly—$aa^{25}$—$aa^{26}$$aa^{27}$—$aa^{28}$—$aa^{29}$—cys—
—cys—$(aa^{32})_c$—w wherein:

Z is bonded to the terminal amino and may be an acyl group, usually acyl of from to 1 to 6 carbon atoms, particularly having an amino substituent, more particularly alpha-amino, e.g. amino acid, alkyl of from 1 to 3 carbon atoms, usually methyl or a protective group e.g. t-butyloxycarbonyl;

aa intends amino acid and the superscript the position of the amino acid, with the proviso that there may be an additional amino acid between $aa^9$ and the cys which would otherwise be $aa^{10}$, with all of the subsequent superscripts increased by one digit when counting for the actual composition, both in the above formula and in the subsequent definitions; the additional amino acid immediately after $aa^9$ will be an aliphatic amino acid, particularly having an alkyl group of from 1 to 5 carbon atoms, more particularly leucine; and amino acid 1 is an aliphatic neutral amino acid, where the amino acid is an unsubstituted aliphatic amino acid of from 2 to 6 carbon atoms;

amino acids 7 and 25 are either unsubstituted aliphatic amino acids or basic amino acids;

w is the terminal hydroxyl, amino, or a peptide of from one to six, usually one to three, more usually one to two, amino acids, having a basic aliphatic amino acid, arg or lys, at the N-terminus, where the amino acids may be added to enhance one or more properties of the oligopeptides;

a, b and c are 0 or 1;

the remaining amino acids are neutral, acidic, basic, polar, aromatic or heterocyclic amino acids.

The neutral amino acids, namely the unsubstituted aliphatic amino acids glycine and alkyl substituted glycines, have alkyl groups of from 1 to 5 carbon atoms, i.e., alanine, proline, hydroxyproline, valine, leucine and isoleucine, and the chalcogen substituted amino acids have oxy and mercapto substituents, particularly methylthio, i.e., serine, threonine, cysteine and methionine (usually cysteine will not be included in this grouping).

The acidic amino acids are aspartic and glutamic acid.

The basic amino acids are the aliphatic amino acids arginine and lysine.

The polar amino acids are asparagine and glutamine.

The aromatic amino acids are phenylalanine, tyrosine and tryptophan.

The aromatic heterocyclic amino acids are histidine.

The various amino acids may be tabulated as follows:

| aliphatic neutral | |
|---|---|
| non-polar | G, A, P, V, I, L |
| polar | S, T, C, M, N, Q |
| acidic | D, E |
| basic | K, R |
| aromatic | F, H, W, Y |

Polypeptides of interest have the amino acids of the above formula as follows:

Amino acids 1, 7, 11, 13, 21, 23, 25, 26, 28, and w are aliphatic amino acids, wherein amino acids 1, 11 and 28 are neutral amino acids, either non-polar or polar; amino acids 1, 7, 13, 21, 23, 25, 26 and w are aliphatic non-polar or polar, particularly 1, 7, 25 and 26 being non-polar and 23 being polar, preferably 11, 13, 21, 26 and 28 being non-polar; or basic, particularly arginine, with 25 preferably being arginine;

amino acids 4, 9, 12, 17, 22 and 27 being aliphatic neutral or aromatic amino acids, preferably 9 and 12 are aliphatic and 27 is aromatic; amino acids 8, 16, 29 and 32 being other than acidic amino acids; preferably amino acid 8 being aliphatic, amino acid 16 being basic, particularly arginine, and amino acid 29 being other than basic, amino acid 32, when present, preferably being basic or aromatic but may also be neutral aliphatic; and amino acid 19 being other than basic, preferably being aromatic or aliphatic polar;

amino acid 2 may be any amino acid, including aliphatic or aromatic, preferably aliphatic non-polar or acidic;

where w is preferably basic or an hydroxyl group.

A preferred group of polypeptides has:
$aa^1$ val or gly;
$aa^2$ ala, val, ile, arg, asp, ser or phe;
$aa^4$ ala, val, thr or tyr;
$aa^7$ basic amino acid, particularly arg and lys, gly or ile;
$aa^8$ ala, arg, gln, pro or phe;
$aa^9$ ala, leu (includes 2leu), phe or ser;
$aa^{11}$ leu, ile, pro, ser or gly;
$aa^{12}$ ala, pro, asn, lys, phe or ser;
$aa^{13}$ arg, leu, ser or gly;
$aa^{16}$ arg, phe or ala;
$aa^{17}$ ala, ser, ile or tyr;
$aa^{19}$ phe, tyr, asp, thr or ser;
$aa^{21}$ arg, lys, ile or thr;
$aa^{22}$ ile, val or tyr;
$aa^{23}$ arg, asn or gln;
$aa^{25}$ arg, ala or val;
$aa^{26}$ leu, ile or arg;
$aa^{27}$ his, tyr, trp or phe;
$aa^{28}$ pro, ala, val or thr;
$aa^{29}$ leu, arg or phe;
$aa^{32}$ arg, tyr, trp, ser or pro; and
w 0-2 arg, particularly 1 to 2.

Usually, there will be not more than six, and usually not more than two acidic amino acids, usually from one to two acidic amino acids, in the preferred compositions. Particularly among the non-primate, only one oligopeptide will have four aromatic amino acids, particulary phe and tyr, usually two each, while among the primate the aromatic amino acids will vary from 5 to 6 amino acids, particularly up to 4 tyrosines, and from 0 to 2 phe and trp each, more particularly 3 tyrosines, 2 tryptophans and 1 phenylalanine.

Of particular interest is $aa^8$ being neutral aliphatic of from 2 to 6 carbon atoms, particularly A or P; $aa^9$ being neutral aliphatic of from 2 to 6 carbon atoms, particularly A or L; $aa^{11}$ being neutral aliphatic of from 3 to 6 carbon atoms, particularly I or L; $aa^{12}$ being neutral aliphatic of from 2 to 5 carbon atoms, particularly A or P; $aa^{16}$ being basic aliphatic, particularly R; $aa^{26}$ being neutral aliphatic, particularly I or L; $aa^{27}$ being aromatic, particularly H or W; and $aa^{28}$ being neutral aliphatic of from 2 to 5 carbon atoms, particularly A or P.

One group of compounds coming within this invention will have the following formula:

wherein:

$Z'$ is methyl, acetyl or other amino capping group, the $Z'$ indicating the N-terminus of the oligopeptide, there being zero to two $Z'$ groups;

m is 0 or 1;

amino acids are designated as aa and their position in the oligopeptide indicated by the super Arabic number, where the amino acids 1, 2, 4, 8, 9, 11, 17, 22, 26, and 29 are all neutral amino acids, usually resulting in hydrophobic regions in the polypeptide, being aliphatic amino acids having either hydrogen or an alkyl group of from one to five carbon atoms at the alpha position or having a chalcogen substituent, which is generally hydroxy or methylthio;

amino acids 12, 27 and 28 are heterocyclic, with 12 and 28 being proline or hydroxyproline and 27 being histidine;

amino acid 19 is an aromatic amino acid, particularly phe; and amino acid 13 is either an aliphatic amino acid as described above or a basic amino acid, particularly either leu or arg.

Of particular interest are amino acids 4, 8 and 17, being either glycine or alanine, with the remaining of the neutral amino acids being the aliphatic amino acids valine, leucine or isoleucine.

Another group of compounds of particular interest has the following formula:

wherein:

$Z'$ has been defined previously;

$aa^2$ and $aa^{12}$ are chalcogen substituted amino acids, particularly ser or phe;

$aa^7$ is arg or gly;

$aa^9$ is phe or leu-leu (2leu);

$aa^{17}$, $aa^{19}$, and $aa^{28}$ are chalcogen substituted amino acids, particularly the hydroxy substituted amino acids ser and thr, particularly with $aa^{17}$ and $aa^{19}$ being ser and $aa^{28}$ being thr; and

$aa^{22}$ is an aliphatic amino acid of from 5 to 6 carbon atoms, particularly val or ile;

$aa^{29}$ is leu;

where the order in which the amino acids are named indicates the preferred association in the polypeptide.

The next oligopeptides of interest have thirty-four amino acids, have the conserved amino acids, where $aa^3$, $aa^5$, $aa^{10}$, $aa^{20}$, $aa^{30}$ and $aa^{31}$ are cys; $aa^6$, $aa^{15}$ and $aa^{33}$ are arg; $aa^{14}$ is glu; and $aa^{18}$ and $aa^{24}$ are gly, where there is a repeated amino acid at $aa^9$, in effect $aa^9$ and $aa^{9a}$ being neutral amino acids, particularly leu. Otherwise, the amino acids vary widely.

The remaining oligopeptides of interest are of the following formula:

wherein b is 0 or 1 and $aa^2$ is an aliphatic amino acid, particularly neutral non-polar of from 2 to 3 carbon atoms or acidic, more particularly alanine or aspartate.

A preferred group of oligopeptides of this invention related to peptides from alveolar macrophages has the following formula:

A preferred group of polypeptides related to polypeptides of rabbit neutrophils has the following formula:

where the particular position of the amino acid above or below the line does not intend that those amino acids should be taken together, rather they may be interchanged, but the positions indicate a preferred composition.

Another group of polypeptides related to polypeptides of rabbit neutrophils has the following formula:

—cys—arg—(arg)$_{0-1}$ where the same limitations concerning the positions above and below apply as indicated for the previous formula.

Quite evidently, one or more of the various amino acids may be exchanged for a different amino acid, without detrimentally affecting the biological activity of the oligopeptides. Furthermore, fragments may find use in providing for antimicrobial activity and avoiding the necessity of preparing a 32 or 33 amino acid oligopeptide. Furthermore, while the naturally occurring amino acids are the L-stereoisomers, it is known that one can obtain advantages by replacing one or more glycines or alanines with the unnatural D-alanine to resist degradation.

Another modification is that available carboxylic acid groups may be modified by amidification with ammonia or low molecular weight amines, e.g. alkylamines of from one to three carbon atoms, particularly methylamine. Furthermore, the terminal amino group may be modified by acylation, e.g. acetylation, alkylation, particularly with lower alkyl groups of from one to three carbon atoms, more particularly methyl, or with linking groups to link to another molecule, such as a protein or non-proteinaceous molecule. Convenient linking groups are dialdehydes, dicarboxylic acids, etc. Other available amino groups may also be sites for linking. Other modifications include the replacement of one or more arginines with lysines and glutamic acid with aspartic acid and vice versa.

The compounds are shown to have activity against a wide variety of microorganisms, such as bacteria, both Gram- positive and -negative, fungi, protozoa and viruses. Different compositions will have differing degrees of activity toward different organisms. The compositions can have opsonin activity, aiding in the phagocytosis of invading pathogens.

The oligopeptides may be used in a wide variety of compositions, depending upon their purpose. For example, small amounts of the oligopeptides may be combined with other proteins to act as preservatives to protect the proteins against bacterial degradation. Alternatively, the subject compositions may be used as preservatives and disinfectants in a wide variety of formulations, such as contact lens solutions, ointments, shampoos, medicaments, foods, and the like. The amount of the oligopeptide which is employed may be varied depending upon the nature of the other components, the degree of protection desired, and the use of the composition. Usually, the concentration will be at least about 0.01 weight percent and not more than about 5 weight percent.

Where the oligopeptides are to be used as antimicrobial agents, they can be formulated in buffered aqueous media containing a variety of salts and buffers. The salts will for the most part be alkali and alkaline earth halides, phosphates, and sulfates, e.g. sodium chloride, potassium chloride or sodium sulfate. Various buffers may be used, such as citrate, phosphate, HEPES, Tris, or the like, to the extent that such buffers are physiologically acceptable to the host which is being treated with the oligopeptides.

The salts will be generally present in from about $10^{-6}$ to about $5\times10^{-2}$ M. Ionic strength will generally range from about $10^{-6}$ to about 0.01, and usually from about $10^{-5}$ to about $5\times10^{-3}$. The pH will generally range from about 6.5 to 8.0, more usually from about 6.5 to 7.8, with the effect attenuating with decreasing pH. In some applications, the oligopeptides will be dissolved in physiologic buffers.

Various excipients or other additives may be used, where the compounds are formulated as lyophilized powders, for subsequent use in solution. The excipients may include various polyols, inert powders or other extenders.

Depending on the nature of the formulation and the host, the subject compounds may be administered in a variety of ways. The formulations may be applied topically, by injection, e.g., intravenously, intraperitoneally, nasopharyngeally, etc.

The subject oligopeptides can be obtained by synthesis, from alveolar macrophages and from polymorphonuclear leukocyte lysosomes. The subject cationic oligopeptides may also be found in other phagocytotic cells. The compositions can be obtained free of other materials present in their naturally occurring environment and can be used individually or in combination in any ratio.

The subject compositions can be obtained in purities of greater than about 99 weight percent, being free of cellular debris and host cell components which may be detrimental to the intended use of the subject compounds. Depending upon the method of preparation, small amounts of contaminants may be present from the mammalian cell source, usually not exceeding about 5 weight percent. For many applications, the purity will not be a significant factor. Where the polypeptides are made by synthetic means, a portion of the polypeptides will be shorter than the desired sequence and may differ in retaining blocking groups. Where hybrid DNA technology is employed lower unicellular microorganism debris or components of such organisms may be present, generally in less than 1 weight percent, usually in less than about 0.01 weight percent.

The alveolar macrophages may be obtained by lavaging the lung in situ after the animal is sacrificed by a toxic injection e.g. sodium pentobarbital. The lavage fluid is conveniently a supplemented phosphate-buffered saline having a pH in the range from about 7 to 8. The fluid is introduced serially to remove free macrophages and the washings combined and purified to remove cells other than the cells of interest. The total number of granulocytes is reduced to less than about 1% of the total number of cells. The number of macrophages is enhanced by injecting the mammalian host with complete Freund's adjuvant about 3 to 4 weeks before sacrificing the host. The cells are homogenized in an aqueous sucrose medium, generally from about 0.3 to 0.4 M, unbroken cells and nuclei removed by centrifugation and after dilution, the homogenates are centrifuged at about 25–30,000×g at 4° C.

The fungicidal and other acid-soluble proteins are extracted using citrate or acetate, at about 0.005 to 0.1 M, pH 2.5–3. After extraction, the solution is centrifuged again at about 25–30,000×g and the protein collected.

After concentration, the protein fraction is dialyzed against an appropriate buffer, followed by purification by gel filtration and gel electrophoresis, particularly with a polyacrylamide gel having a high amount of polyacrylamide, usually from about 12 to 18%, preferably about 15%. Also included in the gel is about 2 to 6 M urea, preferably about 2.5 to 5 M urea. The cationic proteins may be further purified by electro-elution using 0.5–2% acetic acid buffer containing 5–8 M urea.

The neutrophils are obtained substantially platelet and red cell free. The neutrophils are homogenized, cellular debris removed and the granule rich supernatant centrifuged to promote a granule containing pellet. The pellet is extracted with aq. acetic acid (5–20%), the extract concentrated and then chromatographed, employing gel permeation chromatography, eluting with aq. acetic acid (1–10%). The antimicrobial rich fractions may be further purified with an ion-exchange-HPLC or directly purified with a reverse phase HPLC using an acetonitrile gradient in 0.1% aqueous trifluoroacetic acid.

The following examples are offered by way of illustration and not by way of limitation.

EXPERIMENTAL

Materials and Methods

Extraction of lysosome-rich fraction.

Elicted rabbit alveolar macrophages were purified ($\leq 1\%$ granulocytes), and subcellular fractions were prepared as previously described (Patterson-Delafield et al., *Infection and Immunity* (1980) 30:180–192, which disclosure is incorporated herein by reference). A 27,000$\times$g fraction, derived from approximately $10^9$ purified macrophages, was extracted with 10 ml of 0.1 M citric acid by stirring the suspended organelles for 2 h at 4° C. The preparation was centrifuged at 27,000$\times$g for 20 min at 4° C., and the sediment was extracted as before. The combined supernatants contained approximately 2 mg of protein per $10^8$ macrophages. The citric acid extracts were concentrated to approximately 1 ml by using an Amicon ultrafiltration unit with a UM 2 Diaflo membrane (Amicon Corp., Lexington, Mass.).

Precipitation of cationic proteins.

The concentrates were dialyzed against two changes, 1 L each, of 0.05 M HEPES buffer (N-2-hydroxyethylpiperazine-N'-2-ethanesulfonic acid; Sigma Chemical Co., St. Louis, Mo.), pH 7.5, for 24 h at 4° C. This yielded a white, flocculent, biologically active precipitate, the "HEPES precipitate," which was recovered by centrifugation at 27,000$\times$g for 20 min at 4° C. Neither increasing the concentration of HEPES buffer (0.01 to 0.1 M) nor increasing the dialysis time (up to 72 h) increased the quantity of the precipitate. The HEPES precipitate was dissolved in 0.1 M HCl and dialyzed against two changes, 1 L each, of 0.01 M HCl for 24 h at room temperature. Dialyzed HEPES precipitate withstood storage at $-20°$ C. for at least 2 months without losing microbicidal activity. Occasionally, a translucent precipitate, insoluble in 0.1 M HCl, appeared after freezing and thawing. This was removed by centrifugation without concomitant loss of microbicidal activity.

Gel filtration.

Dialyzed HEPES precipitate (1 ml, 2 to 3 mg of protein) was applied to a plastic column (1.2 by 28 cm) containing Bio-Gel P-10, 50–100 mesh (Bio-Rad Laboratories, Richmond, Calif.) that had been equilibrated at room temperature in 0.01 M HCl. Loading and elution were accomplished at a constant linear flow rate, 6 cm/h, of 0.01 M HCl, and 1 ml fractions were collected. The effluent was monitored by measuring its optical density at 215 nm ($OD_{215}$) and $OD_{225}$ in a Gilford Model 222A spectrophotometer and then calculating the difference ($OD_{215}-OD_{225}$) Column fractions were also examined for fungicidal activity (see below). The single candidacidally active peak (peak 3) was pooled, lyophilized (this removed the HCl), suspended in 1 ml of water, and stored at $-20°$ C. Preparations destined for subsequent microbicidal testing were stabilized by adding 0.1 mg of crystalline bovine serum albumin per ml before freezing. Such stabilized preparations retained full microbicidal activity for several months despite repeated freeze-thawing. Fractions to be further purified were stored without bovine serum albumin.

Fungicidal activity of column eluates was monitored by minor modifications of a dye exclusion assay (Lehrer et al., ibid (1975) 11:1126–1234). Briefly, *C. parapsilosis* was grown for 48 h in tryptose phosphate broth (Difco Laboratories, Detroit, Mich.) at 32° C., harvested by centrifugation, and washed three times with sterile distilled water. The fungi were adjusted to $2.5\times10^7$ cells per ml in 0.1 M sodium citrate buffer, pH 6.3. A 50 $\mu$l sample of *C. parapsilosis* suspension was added to 10 $\mu$l of each column eluate fraction in a microtest plate (no. 3040; Falcon Plastics, Oxnard, Calif.) and incubated overnight at room temperature. Then 30 $\mu$l of an aqueous solution of trypan blue (0.2%) and eosin (0.1%), pH 6.4, was added to each well. After 1 h, the percentage of stained yeast cells was determined by examining wet mounts microscopically.

Polyacrylamide gel electrophoresis.

Analytical-disc native tube gels were cast with 15% acrylamide and electrophoresed at pH 4.3, 2 mA/gel, by using the procedure described in Lehrer et al., supra. Long urea gels, as described by Panyim and Chalkley, *Biochemistry* (1969) 8:3972–3979, which disclosure is incorporated herein by reference, were used for the final purification step. Briefly, 15% polyacrylamide gels (0.5 by 25 cm) containing 2.5 M urea were polymerized with ammonium persulfate and pre-electrophoresed at 2 mA/gel for 18 h with 2.5 M urea in 0.9 M acetic acid. After pre-electrophoresis, a stacking gel (0.4 ml) containing 2.5 M urea was photopolymerized with riboflavin as described by Reisfeld et al., *Nature* (London) (1962) 195:281:283. Samples applied to the urea gels contained 100 $\mu$g (Lowry protein) of the fungicidal proteins eluted from the Bio-Gel P-10 column, 10% (vol/vol), glycerol, 2.5 M urea, and 0.001% methyl green as tracking dye. Electrophoresis, 2 mA/gel, was performed until the dye front was 1 cm from the bottom of the gel. Analytical gels were stained for 1 h in 0.2% amido black dissolved in water containing 45% methanol and 9% acetic acid, and destained, by diffusion, in the same solvent. Alternatively, they were stained by the rapid Coomassie blue G-250 method of Reisner et al., *Anal. Biochem.* (1975) 64:509–516.

Localization of protein bands in preparative urea gels.

After electrophoresis, the gels were removed from their tubes and quartered longitudinally. This indicator strip was stained with Coomassie blue G-250 until the protein bands were visible (a few minutes). Approximate $R_f$'s for microbicidal cationic proteins 1 and 2 (MCP 1 and MCP 2) were 0.82 and 0.78, respectively.

Using the stained gel slice as a guidestrip, a 2 cm section from the unstained gels containing the two protein bands was removed and sliced transversely into 2 mm sections that were individually immersed in 250 $\mu$l of water. After 12 h, 50 $\mu$l of the eluted proteins plus 10 $\mu$l of 0.1 M NaHCO$_3$ was re-electrophoresed on small analytical gels and stained to localize the bands. Gel eluates containing a single protein species were appropriately pooled and frozen. Eluates containing mixtures of the two proteins were re-electrophoresed on long urea gels and reprocessed as above. The pooled MCP 1 and MCP 2 acrylamide segments were separately pulverized and thoroughly eluted by twice agitating the suspension at room temperature for 12 h with 5 ml of water. The gel pieces were removed by centrifugation, washed twice with water, and filtered through an Amicon XM-100 membrane. The filtrates were combined and dialyzed against two changes, 1 L each, of 1 mM HCl for 24 h at room temperature. The dialyzed proteins were concentrated to approximately 1 ml in a Speed Vac concentrator-100 (Savant Instruments, Inc., Hicksville, N.Y.) and stored at $-20°$ C.

Densitometry.

MCP 1 and MCP 2 (eluted from 2.5 M urea gels) and hen egg white lysozyme were quantitated by gel densitometry. The protein concentration of the individual cationic protein samples was measured by the method of Lowry et al., *J. Biol. Chem.* (1951) 193:263–275, with egg white lysozyme, $(E_{281.5}^{1\%}=26.4)$ as a standard. The proteins were applied to analytical 15% acrylamide gels (pH 4.3), electrophoresed, stained, and destained as described for amido black. The gels were scanned in a Gilford gel scanner, Model 2520, at 580 nm at a scan rate of 0.5 cm/h and a chart speed of 150 cm/h. Densitometric traces were measured with a Keuffel & Esser model 62 0000 compensating polar planimeter (Keuffel & Esser, Morristown, N.J.). Estimates of concentration were done on gels whose samples were in the linear portion of the densitometric standard curve, as described below.

Amino acid analysis.

Amino acid analyses were performed on a Durrum D-500 automatic amino acid analyzer by the method of Moore and Stein, *Methods Enzym.* (1963), 6:819, employing single-column methodology. Triplicate samples were hydrolyzed in 1.0 ml of 6 N HCl containing 20 μl of 5% (wt/vol) phenol for 24 h at $110°\pm2°$ C. in vacuo. Half-cystine content was determined as cysteic acid on separate duplicate samples after performic acid oxidation (Moore, *J. Biol. Chem.* (1963) 238:235–237). Threonine and serine contents were corrected upward 5 and 10%, respectively, for destruction during acid hydrolysis. Tryptophan content was not determined.

Microorganisms and microbicidal assays.

*Salmonella typhimurium* SL 4045 and *Listeria monocytogenes* were grown as previously described (Patterson-Delafield, supra). *C. albicans* 820 was cultivated in Sabouraud dextrose broth (BBL Microbiology Systems, Cockeysville, Md.). Overnight cultures (5 ml) were grown in liquid medium with agitation at 37° C. A 1:50 dilution was made into 50 ml of prewarmed medium contained in a 125 ml Ehrlenmeyer flask, and this subculture was shaken at 37° C. until the midphase of exponential growth was attained. The mid-log-phase organisms were recovered by centrifugation, washed three times in assay buffer (see below), and suspended to a final cell density of $5\times10^6$/ml in that buffer. The assay buffer (ionic strength, 0.02) contained 0.01 M sodium citrate, $5\times10^{-4}$ M MgSO$_4$, $1.5\times10^{-4}$ M CaCl$_2$, and 0.056 M glucose (pH 6.3). Reaction mixtures (0.5 ml) contained $5\times10^5$ colony-forming units in buffer at 37° C. Microbicidal proteins were added last. Timed samples were removed and serially diluted in 0.05 M phosphate buffer (pH 7.4) containing the aforementioned additives. The dilution buffer was found experimentally to block the lethal expression of unadsorbed macrophage cationic proteins, allowing precise timing of the kinetics of microbicidal activity. The ionic strength of all buffers was measured with a Yellow Springs Instruments model 31 conductivity bridge, using NaCl solutions as standards.

An alternative purification procedure follows, which provides for substantially pure products.

Purification of MCP 1 and MCP 2.

Lyophilized protein (6.6 to 9.6 mg) was dissolved in 3.0 ml of a solution of 1.0% acetic acid containing 4.5 M urea (Pierce Chemical Co.). This material was subjected to preparative acid-urea polyacrylamide gel electrophoresis in 3 mm×160 mm×200 mm slab gels, using the system described by Panyim and Chalkley, *Arch. Biochem. Biophys.* (1969) 130:337–346. The resolving gel, of 12.5% acrylamide, was surmounted by a shallow (15 mm), 7.5% acrylamide spacer gel that had been polymerized around a 3 mm×18 mm×140 mm sample-well former. The use of this lower density spacer gel was found to be critical for avoiding band 'tailing' at the resolving gel's edges. Preparative gels contained 5.0 M urea and had an acrylamide/bis-acrylamide ratio of 37.5:1. The gels were pre-run overnight at a constant 125 V with 0.9 M acetic acid as the reservoir buffer, using clearance of methyl green (Matheson, Cole and Bell) to verify completeness of the process. The sample was electrophoresed toward the cathode at constant voltage, 125 V, for approximately 7 h until its methyl green dye (2 μg/ml of sample) had electrophoresed off the gel. The gel was then immersed for 30 sec in a 0.1 N NaOH solution containing 0.25% (w/v) eosin Y (Sigma Chemical Co.), and then rinsed for 30 sec in distilled water. This brief exposure to eosin disclosed several bright orange bands, the most prominent of which corresponded to MCP 1, MCP 2, and lysozyme. The gel regions containing these bands were precisely cut from the slab with a pizza slicer (Thrifty Drug and Discount, Inc.) and stored at $-20°$ C.

After approximately 2 ml of a 7.5% acrylamide gel solution had been polymerized in a 15 ml conical plastic centrifuge tube (Corning Glass Works), the tube's bottom was cut off about 1 cm from the end. The acrylamide plug, supported by the slanting walls of the tube, remained. After several such tubes were pre-electrophoresized for 2 h at 150 V, their plug-containing tips were fitted with short sections, approximately 8 cm long, of dialysis tubing completely filled with 1% (v/v) acetic acid. After slices of the eosin-stained gel had been inserted into the plugged electro-elution tubes, they were filled to within 0.5 cm from the top with 1% acetic acid containing 6.0 M urea. Reservoir buffer, 1% acetic acid, was layered about the acetic acid/urea solution, and finally poured into the upper and lower electrophoresis chambers. Electrophoresis was performed at 100 V for 16 h. During this electro-elution, the eosin migrated anodally, and the peptides moved cathodally into the dialysis sac. The current was reversed for the final 2 min of the procedure to abet recovery of any protein or peptide adsorbed to the dialysis membrane. The electro-eluted material was recovered, transferred to fresh tubing, dialyzed against 0.1% acetic acid, and stored at $-20°$ C., or lyophilized.

Analytical Polyacrylamide Gel Electrophoresis.

The 1 mm analytical slab gels were stained for 1 h in a solution containing 0.1% Coomassie brilliant blue (Sigma) in acetic acid/methanol/water (10:30:60) and destained by diffusion in acetic acid/methanol/water (10:10:80). The acid-urea gels were identical to those described above with exception that a multiple sample well former was used.

The efficiency of the purification scheme was assessed quantitatively as follows. Briefly, analytical acid urea gels were loaded with various amounts of MCP 1 and MCP 2 standards as well as the crude starting material. After electrophoresis, gels were stained as described above, and the Coomassie-stained MCP 1 and MCP 2 bands were cut from the gel and eluted in 2.0 ml of 60% formic acid for 24 h (Gibson and Gracy, *Anal. Biochem.* (1979) 96:352-354). The amount of Coomassie stain eluted was measured spectrophotometrically at 650 nm, and bore a linear relationship to the amount of MCP loaded on the gel, in the range of 1 to 10 μg of peptide per band.

Estimations of Molecular Weight.

The method of Hedrick and Smith (*Arch. Biochem. Biophys.* (1968) 126:155-164) was used to estimate the molecular weight of non-reduced MCP 1 and MCP 2. Briefly, the peptides and non-reduced standards were electrophoresed in a series of acid-urea gels with acrylamide concentrations of 10.0, 12.5, 15.0, 17.5, and 20%. The log of the migration ($R_m$) of MCP 1 and MCP 2, and of the standards was plotted against the acrylamide concentration; the slope (retardation quotient) is related to the protein/peptide molecular weight.

The sodium dodecyl sulfate polyacrylamide gel system described by Shapiro et al. (*Biochem. Biophys. Res. Comm.* (1967) 28:815-820) was employed for molecular weight estimations of reduced MCP 1 and MCP 2, and that of Laemmli (*Nature* (London) (1970) 227:680-685) was used for purity assessment. Prestained, low molecular weight standards (Bethesda Research Laboratories) were used as standards in molecular weight determinations. Samples were reduced by boiling for 5 min in sample buffer containing 2-mercaptoethanol.

Gel Filtration in Guanidine Hydrochloride.

The apparent molecular weights of MCP 1 and MCP 2 were also determined by gel filtration on a 1.5×86.5 cm Bio-Gel P-60 (100-200 mesh, Bio-Rad Laboratories) column equilibrated in 6.0 M guanidine HCl, 0.05 M Tris-HCl, pH 8.52 (Fish et al., *J. Biol. Chem.* (1969) 214:4989-4994). Purified MCP 1 and MCP 2, and calibration standards were reduced with dithiothreitol (DTT) and then carboxymethylated with an excess of iodoacetic acid (Sigma). The labeled peptides were separated from reaction products by passing the mixture over a Bio-Gel P-2 column (50-100 mesh, 1.5 cm×26 cm), equilibrated in 6.0 M guanidine HCl, 0.05 M Tris-HCl, pH 8.52. MCP-containing fractions, which eluted at the void volume, were pooled, and used as such for chromatography on the P-60 column, or dialyzed against 0.1% acetic acid and lyophilized. Reduced and alkylated standards used for calibration were: horse heart cytochrome C (N=104, Sigma), aprotinin (N=58, Sigma), insulin B chain (N=30, Boeringer Mannheim), and insulin A chain (N=21, Sigma), where N=the number of amino acids in the peptide chain. Reduced and alkylated transferrin (MW=90,000), and methyl green were chromatographic indicators of the void and included volumes, respectively. In the case of the reduction and alkylation of MCP 1 and MCP 2, carboxymethylation was performed using [$^3$H]-iodoacetate (New England Nuclear) in order to generate isotopically labeled peptides.

The column was calibrated as described by Fish et al., supra. The method of Porath (*Pure Appl. Chem.* (1963) 6:233-244) was used for determining $K_d$, the distribution coefficient:

$$K_d = \frac{V_e - V_o}{V_i - V_o}$$

where $V_e$ is the position of the standard (or MCP) elution peak, $V_i$ is the included volume, and $V_o$ is the void volume. $K_d$ was determined experimentally using the volume and/or time of peak elution by continuously monitoring the column effluent with an ISCO UA-5 recording absorbance monitor ($A_{280}$) in conjunction with an ISCO Model 328 fraction collector. A standard curve wherein $K_d^{\frac{1}{3}}$ was plotted against $N^{0.555}$ was constructed (Fish et al., supra).

The $K_d$'s for [$^3$H]-MCP 1 and [$^3$H]-MCP 2 were determined by liquid scintillation spectrometry of column effluent fractions, using a Beckman Model LS 330 Liquid Scintillation Counter. Calibration standards, and $V_o$ and $V_i$ indicators were included with each loading of [$^3$H]-MCP 1 or [$^3$H]-MCP 2.

Chemical Analysis of MCP 1 and MCP 2.

MCP 1 and MCP 2 were analyzed for free sulfhydryls by reaction with 5,5'-dithiobis(2-nitrobenzoate) (DTNB) in 6.0 M guanidine hydrochloride, 0.05 M Tris-HCl, pH 8.52 (Glazer et al. (1975) *Chemical Modification of Proteins* (Work, T. S. and Work, E. eds.) North Holland/American Elsevier). Carbohydrate content of MCP 1 and MCP 2 was determined by the phenol-sulfuric acid procedure (Dubois et al., *Anal. Chem.* (1956) 28:350-356). The tyrosine and tryptophan content of MCP 1 and MCP 2 was determined spectrophotometrically by the method of Edelhoch (*Biochem* (1967) 6:1948-1954). Protein determinations using the Lowry (*J. Biol. Chem.* (1951) 193:262-275), o-phthalaldehyde (Robrish et al., *Anal. Biochem.* (1978) 84:196-204), and $A_{215} - A_{225}$ (Murphy and Kies, *Biochem. Biophys. Acta.* (1960) 45:382-384) methods were compared. The absorbance spectra of MCP 1 and MCP 2 were recorded in a Beckman Model 24 dual beam spectrophotometer. For this analysis, the peptides were lyophilized and dissolved in 1 mM sodium acetate, pH 6.3.

The various methods of protein determination gave values which varied by no more than about 20% between methods. The average values of the various methods most closely approximated those determined by the microbiuret assay, which was the chosen method thereafter.

In the urea-containing SDS-PAGE system of Shapiro et al., the apparent molecular weights of reduced MCP 1 and MCP 2 was estimated to be 4700 and 4300 daltons, respectively. The observation that the apparent molecular weight did not decrease under reducing conditions suggest that the peptides exist as single polypeptide chains. Molecular weight determinations by gel chromatography of reduced and carboxymethylated MCP 1 and MCP 2 in 6.0 M guanidine hydrochloride confirmed the results. The data showed that the reduced and carboxymethylated MCP 1 and MCP 2 eluted at the same $V_e$. The elution peaks of both MCP 1 and MCP 2 were symmetrical, each corresponding to a single polypeptide chain with an average integer value of 41 amino acids. The molecular weights of MCP 1 and MCP 2 were calculated, based on the mean residue weight, $\overline{M}_o$ to be 4476±19 and 4395±15, respectively. The absence of tryptophan and tyrosine was indicated spectrophotometrically.

Titration of MCP 1 and MCP 2 with DTNB in 6.0 M guanidine hydrochloride showed no evidence of oxidation, indicating the absence of available sulfhydryl groups. This observation is consistent with the other observation that neither MCP 1 nor MCP 2 reacted with iodoacetate without previous reduction. Neither MCP 1 nor MCP 2 contain any carbohydrate as assessed by the phenol-sulfuric acid assay. The test was performed under conditions whereby 0.5 glucose-equivalents per molecule of MCP would have been detected.

The neutrophil proteins (NP) were prepared substantially the same way as the macrophage proteins, with the following differences. Rabbit peritoneal neutrophils were extracted with 0.1 M citric acid at 4° C. for 24 h at a concentration of about cells per 50 ml. The solution was then dialysed and electrophoresed as described for the MCP compounds, yielding five fractions. The fractions were then further purified and the fraction having 3A and 3B separated into two pure components by HPLC. A reverse phase C18 (Vidak) HPLC column was employed, eluting with solutions having from 2 to 28% by volume of 0.025% trifluoroacetic acid in acetonitrile diluted with an aqueous 0.025% trifluoroacetic acid solution. Elution took 30 min yielding pure (>99% pure) neutrophil proteins which were lyophilized and sequenced.

The sequences of the oligopeptides demonstrating the conserved portions in boxes are set forth in Table I, where the second arg may be removed by tryptic or carboxypeptidase digestion.

A modified procedure was employed as follows, for obtaining the cationic proteins in a pure state.

Peptide Purification.

The citric acid-soluble material obtained by extracting the 27,000×g postnuclear sediment or the whole sonicate was dialyzed exhaustively against 0.1% acetic acid in tubing (Spectrum Industries, Los Angeles, Calif.) with a molecular weight cutoff of 3500, lyophilized, and redissolved at 2–6 mg of protein/ml in 1.0% acetic acid containing 3.0 M urea. 0.5–1.5 ml samples of this material were electrophoresed on acidic, urea-containing polyacrylamide gels, 3×160×220 nm in size, for approximately 9 h. Gels were subsequently immersed in a solution of 0.25% (w/v) eosin Y (Sigma, St. Louis, Mo.) in 0.1 N NaOH for 30 sec, thus disclosing up to 25 transverse magenta-staining bands of protein. Gel strips containing the five most cathodal bands were individually excised from eight simultaneously run gels, pooled, and subjected to electrophoretic elution. The eluted peptides were dialyzed against 1.0% acetic acid and lyophilized. Each of the electrophoretically fractionated peptides was subjected to further purification by reversed phase high performance liquid chromatography (RP-HPLC) on a Spectraphysics SP 8700 system equipped with a Rheodyne 7125 sample injector (2.0 ml loop), a Waters 450 variable wavelength detector, a Kipp and Zonen BD 40 recorder, and a large pore (330 A) 1.0×25.0 cm Vydac 218 TP C-18 column. Water-/acetonitrile gradients containing 0.025% trifluoroacetic acid (TFA) were used in elution. A 0.46×25 cm C-18 column (μBondpak, Waters) was used for some analytical RP-HPLC runs.

Analytic Methods.

Peptide purity was evaluated using RP-HPLC, acid-urea PAGE, and sodium dodecyl sulfate (SDS) PAGE. Estimations of peptide molecular weights were made based on the migration of purified samples in SDS-PAGE (Selsted et al., *J. Biol. Chem.* (1983) 258:14485–14489).

The subject compounds MCP 1 and MCP 2 were found to be effective against *C. albicans, L. monocytogenes* and *S. typhimurium* in order of decreasing effectiveness. At an ionic strength of 0.024, there was no significant change in effectiveness over the pH range from about 5.0 to 8.0 for *C. albicans*. In contrast, bacterial species were most susceptible to MCP-1 and MCP-2 between pH 6.5–8.0 and they showed substantially less susceptibility below pH 6.0. Ionic strength also influenced the peptides' direct antimicrobial activity. At higher pH levels, a precipitate forms. While pH did not have a significant effect, ionic strength did. In a representative experiment, 3 μg of a mixture of the two compounds per ml reduced the number of viable *C. albicans* by over 99% in 5 min under standard conditions, as described previously. This was unaffected in the presence of 0.1 M mannitol in the assay buffer. However, increasing the ionic strength to 0.05 reduced killing to approximately 60% and increasing it to 0.08 prevented candidacidal activity. Of the three alkali metal halides employed, no difference was observed. Heating at 100° C. for 10 min at a concentration of 10 μg/ml in assay buffer did not affect the compound's activity. It was found that MCP 1 is approximately 3–4 times as effective as MCP 2 against *C. albicans*.

The subject peptides were also tested and shown to be effective in restricting replication of viruses in human, rabbit and monkey cells. This effect was demonstrated by two experimental systems. One of these measured the peptides' ability to directly inactivate certain viruses [e.g., Herpes simplex, Type 1 (HSV-1), Herpes simplex, Type 2 (HSV-2), Vesicular stomatitis virus (VSV), etc.] The protocol for testing direct viral inactivation is as follows: Virus stock solutions, containing $10^7$ to $10^9$ plaque-forming units (PFU)/ml are incubated with various concentrations, 1–100 μg/ml, of MCP-1 or MCP-2 for 30 to 60 minutes at 37° C. in appropriate tissue culture (TC) media. Thereafter, the mixtures are serially diluted and plaqued on Vero monkey kidney cells. Exposure of HSV-1 (McIntyre strain) to 100 μg/ml of MCP-1 or MCP-2 for 60 minutes caused the number of PFU/ml to decline from $10^7$ PFU/ml to less than $10^4$ PFU/ml, in contrast to the control which showed little decrease in PFU/ml. MCP-1 and MCP-2 appeared to be equally potent in causing direct viral inactivation. Other viruses susceptible to direct inactivation by MCP-1 and MCP-2 are HSV-2, VSV, vaccinia and influenza A.

Figure 1:
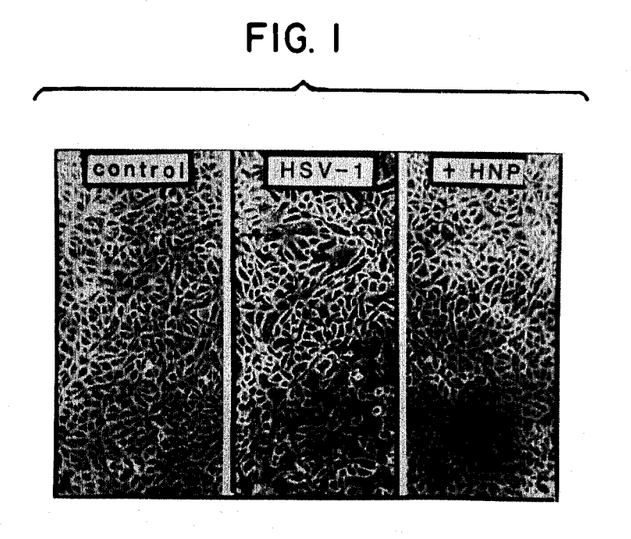
FIG. 1 illustrates the effect of the peptides of the present invention on Vero cells infected with HSV-1.

In addition to direct inactivation, the peptides decrease the replication of viruses including HSV-1, HSV-2, VSV and cytomegalovirus (CMV) in otherwise permissive human fibroblasts (e.g., GM 2504 and MRC-5 cells) or rabbit and monkey kidney cells (Vero). When Vero cells are infected by HSV-1, the infected cells demonstrate prominent cytopathic effects (CPE) consisting of cell rounding with formation of multinucleated cells with premature cell death. When the cells are exposed to HSV-1 in the presence of 25 μg/ml of MCP-1, this CPE is almost completely prevented. These effects are illustrated by FIG. 1, which shows the appearance of Vero cells that are (a) uninfected, (b) infected with HSV-1 (McIntyre) at a MOI of 0.1, and (c) infected with HSV-1 in the presence of 25 μg/ml of MCP-1. The normal appearance of the Vero cells and the prevention of CPE are apparent.

This procedure is also performed quantitatively by the following protocol.

On day one, the cells, either human fibroblasts or monkey kidney, are set up. On day two, samples and interferon-α controls are diluted in TC media. The cells growth medium is replaced with the TC media in which the sample polypeptide or α-interferon (IFN-α) have been serially diluted and the cells exposed to these media overnight. On day three, the media are removed and the cells infected with virus, employing the series at different MOI. After infection, in one series the sample polypeptide containing medium is returned and in another series, fresh TC medium is employed. With VSV the control concentrations were 0.1, 1, and 10 U/ml while with HSV the IFN-α concentrations were tenfold higher.

On day four, the cytopathic effect (CPE) is scored and the incubation is continued until 60–90% of the virus-infected cells manifest CPE (20–27 hours for VSV and HSV-2, 30–38 hours for HSV-1 and 5 days for CMV). At this point in time, the culture fluids were harvested and plaque formation was determined. The virus yields from test samples were compared to control wells.

In representative yield reduction studies, 25 μg/ml of MCP-1 caused a 4 $\log_{10}$ reduction in VSV yield and a 3 $\log_{10}$ reduction in HSV-1 yield, relative to untreated controls. In contrast, IFN-α caused a 0.6 $\log_{10}$ decrease in HSV-1 yield when present at 100 IU/ml and a 6 $\log_{10}$ decrease in VSV yield when present at 10 IU/ml in tests conducted with the human GM 2504 fibroblast cell line.

To test antibacterial action of the polypeptides, the following protocol was employed. Various species at $10^7$ bacterial cells/ml are incubated for 20 min at 37° with 50 μg/ml of the candidate peptide. Colony counts (viable organisms) are made at the outset of the incubation—before addition of the candidate peptide—and after 20 min of incubation with the candidate peptide. The results are found in Table II.

To further demonstrate antibacterial activity the following study was performed. The procedure parallels that reported in Lehrer et al., *Infection and Immunity* (1983) 42:10–14. Fourteen bacterial isolates, as shown in Table III, were cultivated for 16 h at 37° C. in nutrient broth, mixed and subcultured by adding 1 ml to 49 ml of fresh nutrient broth. The subculture was grown at 37° C. for 4 h with shaking to provide mid-logarithmic phase organisms that were washed twice with buffer by centrifugation (2000×g, 10 min), and then quantitated spectrophotometrically at 620 nm, with reference to previously established CFU/Optical Density relationships.

Bacteria were suspended and experiments were performed in 10 mM sodium phosphate buffer, pH 7.4. In some experiments, buffers were supplemented with 0.14 M NaCl ("high" ionic strength). The conductivities of the standard and NaCl supplemented buffers were 1.36 and 12.3 mMHO, respectively, as determined with a Sybron/Barnstead PM-70 CB conductivity bridge. In some experiments, 10 mM phosphate buffer with a pH of 5.8 and conductivity of 1.36 mMHO was used. Peptide "stock solutions" were prepared at 500 μg/ml (microbiuret assay) in 0.01% acetic acid, and stored at −20° C.

Typically, incubation mixtures contained $1 \times 10^5$ bacterial CFU and 5 μg of peptide in 100 μl of buffer. After incubation for 20 min at 37° C., 900 μl of the same buffer was added, and two additional serial tenfold dilutions were made with that buffer. Duplicate 100 μl aliquots from the three serial dilutions were spread over appropriate nutrient agar plates and incubated for 24–72 h to insure full colony development. Killing of microorganisms was expressed as the $\log_{10} N_o/N$, where $N_o$ represented the initial colony count and N represented the colony count after incubation with peptide. There was no significant alteration in colony count when any of the test organisms were exposed to peptide-free buffer for 20 min.

Purification of Human Neutrophil Peptides.

Human neutrophils were obtained in single donor leukopheresis packs from a commercial supplier (Hemacare, Van Nuys, Calif.) and processed within 2 h of harvest. The cells were twice washed of platelets by low speed centrifugation (200×g for 10 min) and resuspension in Dulbecco's phosphate buffered saline at 4° C. Contaminating red cells were removed by a 45 sec cold hyptotonic lysis followed by low speed centrifugation. This left a pellet containing $1-3 \times 10^{10}$ leukocytes, 90% of which were neutrophils, with the remainder consisting mostly of lymphocytes and monocytes. Over 90% of the cells were viable by trypan blue exclusion.

The leukocytes were resuspended in 30 ml of 0.34 M sucrose (pH 7.4) and homogenized in a glass-teflon homogenizer until most cells appeared broken under phase-contrast microscopy. The cell debris and unbroken cells were removed by another low speed centrifugation, 200×g for 10 min, leaving a granule-rich supernatant. The residual cell pellet was subjected to three more cycles of homogenization and centrifugation in 0.34 M sucrose to yield additional granule-rich supernatants. The supernatants were combined and centrifuged at 27,000×g for 30 min at 4° C. The resulting pellets were pooled and extracted overnight in 100 ml of 10% acetic acid at 4° C. This extract was cleared at 27,000×g for 30 min and concentrated to about 10 ml in a vacuum centrifuge (Speed-Vac, Savant Instruments, Inc., Hicksville, NY).

The initial fractionation of the concentrated granule extract was accomplished by gel permeation chromatography with 15 ml on a 137 cm×3.8 cm P-10 Biogel column (Bio-Rad, Richmond, Calif.). Three peptides satisfying our initial search criteria coeluted with HNP1-3 emerging as a late and incompletely resolved series of peaks, monitored at 280 nm. They were named according to their relative cationic mobility on acid urea-polyacrylamide gel electrophoresis (AU-PAGE): human neutrophil peptide (HNP)-1 (greatest mobility), HNP-2 (intermediate mobility) and HNP-3 (least cationic). Separation of HNP-3 from HNP-1 and -2 was accomplished by high performance liquid ion exchange chromatography on a carboxymethylsilica column (Biosil TSK 1EX-535CM, 150 mm×6 mm Bio-Rad, Richmond, Calif.) in 50 mM 0.05 M sodium phosphate/10% acetonitrile, pH 7.0, eluted with a sodium chloride gradient, monitoring by absorbance at 280 nm. (The gradient employed the indicated buffer with 1M NaCl in from 0–40%). This was followed by desalting and purification by reverse phase high performance liquid chromatography (RP-HPLC) over a C-18 alkylsilica column (Vydac, Rainin Instrument Co., Woburn, Mass.) in 0.1% trifluoroacetic acid, with elution by an acetonitrile gradient. HNP-1 was separated from HNP-2 by recycling the mixture on a 150 cm long Biogel P-10/1% acetic acid gel permeation system, followed by RP-HPLC as before. The fractionation was monitored and the purity of each peptide was assessed by AU and SDS-PAGE.

Antibacterial Assays.

The bactericidal activity of human neutrophil peptides was tested against *Staphylococcus aureus* 502A, *Pseudomonas aeruginosa* PA0579, and *Escherichia coli* ATCC 29648. The organisms were maintained or trypticase soy agar plates and organisms from a single colony were inoculated into 50 ml of trypticase soy broth (Difco, Detroit, Mich.) and cultured overnight at 37° C. One ml of this intermediate culture was diluted with 49 ml of fresh nutrient broth and incubated for an additional 18 h at 37° C. A portion of this stationary phase culture was washed with 10 mM phosphate buffer, pH 7.4, and the concentration of CFU/ml was quantitated by measuring its absorbance at 620 nm with reference to previously determined CFU/ optical density measurements. Incubation mixtures contained $1 \times 10^5$ bacterial CFU and 5 μg of HNP1-3 in 100 μl of 10 mM sodium phosphate buffer, pH 7.4. Control mixtures lacked HNP1-3 but contained a small amount of acetic acid (final concentration 0.08 mM), which was used as a vehicle for our HNP stock solutions. This basic incubation mixture was supplemented with various nutrients. Following incubation with HNP1-3 for 2 h at 37° C., timed samples were removed, serially diluted, spread on nutrient agar plates and incubated for 48-74 h to allow full colony development.

Antifungal Assays.

*Cryptococcus neoformans* C-384 (Type C) was maintained on Sabouraud's 2% dextrose agar plates. Test organisms were prepared by inoculating 10 ml of Sabouraud's 2% dextrose broth with a loopful of organisms from a single colony and incubating this culture for 18 h at 37° C. From this intermediate culture, 1 ml was removed and added to 50 ml of fresh Sabouraud's broth that was incubated at 37° C. for an additional 18 h. The test organisms were washed twice by centrifugation in 10 mM sodium phosphate buffer, counted in a hemocytometer and adjusted to the desired concentration in 10 mM sodium phosphate buffer. Incubation mixtures contained $1 \times 10^5$ CFU/ml and 5 μg of HNP1-3 in a final volume of 100 μl. These mixtures were incubated at 37° C. for 20-240 min, and samples were removed, serially diluted and spread on Sabouraud's 2% dextrose agar petri plates for 3-5 days to ensure full colony development.

Antiviral Assays.

The activity of human neutrophil peptides against herpes simplex virus, Type 1 (HSV-1, McIntyre strain) was tested in two systems. The first was qualitative. In these tests, each of the HPLC-purified, lyophilized fractions were dissolved in 100 μl of 0.01% acetic acid. A portion (40 μl) of this solution was mixed with 360 μl of Eagle's minimal essential medium (Grand Island Biologicals, Grand Island, N.Y.) containing 2% fetal bovine serum, 20 mM hepes buffer (pH 7.3), antibiotics (100 units/ml) penicillin and 100 μg/ml streptomycin) and HSV-1 ($1 \times 10^5$ PFU/ml). The final pH of this mixture was 7.25. After 30 min at room temperature, this mixture was placed over Vero cell monolayers in 24-well tissue culture plates and incubated for 24-48 h at 37° C. with periodic monitoring by inverted phase microscopy. Unprotected infected monolayers developed characteristic moderate CPE by 24 h (polykaryon formation and mild cellular rounding) that progressed markedly by 48 h). Fractions containing HNP1-3 were initially detected and their purification followed by the marked protection they afforded from virally-induced CPE.

The second assay was quantitative, and measured by the direct neutralization of HSV-1 by the peptides. For this test, various concentrations of HPLC-purified peptide in 180 μl of normal saline solution were mixed with 20 μl of titered HSV-1 preparations (approximately $4 \times 10^6$ PFU/ml in Eagle's minimal essential medium containing 2% v/v fetal bovine serum and antibiotics) and incubated for 60 min at 37° C. Control mixtures containing only HSV-1 and dilute acetic acid (the vehicle for HNP1-3) in phosphate buffered saline were incubated in parallel at 37° C. At the conclusion of this incubation, the mixtures were serially diluted and viral PFU were titered in triplicate on Vero cell monolayers by standard techniques. In four representative experiments, the mean coefficient of variation (Standard deviation/mean) of this assay procedure was 20.9%.

Immunoperoxidase Staining.

HNP1-3 was conjugated to ovalbumin (Sigma, St. Louis, Mo.) by glutaraldehyde (-16), mixed with complete Freund's adjuvant (Difco, Detroit, Mich.) and used to immunize a rabbit. Sera were fractionated on DEAE cellulose to provide an IgG fraction used for subsequent staining. Preimmune serum, similarly fractionated, served as the control. Slides containing normal human neutrophils were fixed for 10 min in phosphate buffered saline containing 10% formalin, and washed with TBS (20 mM tris, pH 7.5, 500 mM NaCl). To inactivate endogenous peroxidase activity, the slides were treated with 0.1 M periodic acid for 5 min, rinsed with distilled water and treated with 0.02% sodium borohydride for 2 min. The slides were washed with TBS and incubated for 48 h with a 1:500 dilution of rabbit anti-HNP-IgG or preimmune IgG (control) in antibody buffer (AB) consisting of 0.05% Tween 20, 0.01% thimerosal and 1% gelatin in TBS). Following this primary incubation, they were washed with TBS containing 0.05% Tween and incubated for an additional 48 h with a 1:2000 dilution of peroxidase-labeled goat anti-rabbit IgG (Cappell Laboratories, Cochransville, Pa.). After extensive washing, first with TBS/0.05% Tween and then with TBS, the immunoperoxidase stain was developed by placing the slides in TBS/0.015% $H_2O_2$/0.05% 1-chloronaphthol (Bio-Rad, Richmond, Calif.) for 10 min. The slides were washed with water, and counterstained with 0.01% acridine orange to bring out the nuclear morphology.

Antibacterial Activity.

The effects of exposing *Staphylococcus aureus* 502A to HNP1-3 is shown in Table IV. Note that whereas the bacteria were unaffected by the defensins in 10 mM phosphate buffer, addition of either 5 mM phosphate or 1% nutrient (trypticase soy) broth sensitized the bacteria to the peptides. In other experiments it was observed that 0.05 mM glucose was as effective as 5 mM glucose in sensitizing *S. aureus* exposed to HNP1-3 for 2 h, and that the sensitizing effect of 5 mM glucose was fully apparent by 20 min of incubation. Neither 5 mM pyruvate nor a mixture of six amino acids replaced glucose or trypticase soy broth in sensitizing the staphylococci to HNP1-3.

The susceptibility of two gram-negative bacteria to HNP1-3 is shown in Table V. Consonant with the observation on *S. aureus*, neither *P. aeruginosa* nor *E. coli* was killed after exposure to 50 μg/ml of HNP1-3 in 10 mM phosphate buffer, and both were susceptible when the incubation mixture contained 1% trypticase soy broth. In contrast to the experiments with *S. aureus,* addition of glucose had little or no effect in inducing sensitivity to the peptides.

Antifungal Activity.

The activity of HNP1-3 was tested against *Cryptococcus neoformans* C-384. Unlike the aforementioned bacteria, this organism was exquisitely susceptible to HNP1-2 in nutrient-free buffer. Killing was extensive and time-dependent, with a reduction of >3 $\log_{10}$ CFU/ml, relative to control, after 4 h of incubation. Colony counts of the controls remained essentially unaltered during the 4 h incubation period.

Antiviral Effects.

The direct inactivation of herpes simplex virus, Type 1 by HNP1-3 was observed with viral inactivation being biphasic. The initial rapid fall in viral PFU/ml was followed by a more gradual decline that continued for the duration of the experiment (4 h).

persistence is undesirable. The water solubility of the subject compounds permits them to be readily formulated in a wide variety of ways with numerous compositions to provide preservative and disinfectant activity. In addition, the oligopeptides may be prepared so as to have the same or substantially the same amino acid sequence of a particular host, so as to avoid immunogenic problems. The relatively small size of the oligopeptides permits their ready synthesis, either through recombinant DNA or using mechanical automatic synthesizers. Also, the conserved framework allows for substantial variation in composition while still retaining antimicrobial activity against selected organisms.

Although the foregoing invention has been described in some detail by way of illustration and example for purposes of clarity of understanding, it will be obvious that certain changes and modifications may be practiced within the scope of the appended claims.

TABLE I

|       | 1   | 2   | 3   | 4   | 5   | 6   | 7   | 8   | 9   | 10  | 11  | 12  | 13  | 14  | 15  | 16  | 17  | 18  | 19  | 20  |
|-------|-----|-----|-----|-----|-----|-----|-----|-----|-----|-----|-----|-----|-----|-----|-----|-----|-----|-----|-----|-----|
| HNP-1 |     | ala | cys | tyr | cys | arg | ile | pro | ala | cys | ile | ala | gly | glu | arg | arg | tyr | gly | thr | cys |
| HNP-2 |     |     | cys | tyr | cts | arg | ile | pro | ala | cys | ile | ala | gly | glu | arg | arg | tyr | gly | thr | cys |
| HNP-3 |     | asp | cys | tyr | cys | arg | ile | pro | ala | cys | ile | ala | gly | glu | arg | arg | tyr | gly | thr | cys |
| NP-1  | val | val | cys | ala | cys | arg | arg | ala | leu | cys | leu | pro | arg | glu | arg | arg | ala | gly | phe | cys |
| NP-2  | val | val | cys | ala | cys | arg | arg | ala | leu | cys | leu | pro | leu | glu | arg | arg | ala | gly | phe | cys |
| NP-3a | gly | ile | cys | ala | cys | arg | arg | arg | phe | cys | pro | asn | ser | glu | arg | phe | ser | gly | tyr | cys |
| NP-3b | gly | arg | cys | val | cys | arg | lys | gln | 2leu| cys | ser | tyr | arg | glu | arg | arg | ile | gly | asp | cys |
| NP-4  | val | ser | cys | thr | cys | arg | arg | phe | ser | cys | gly | phe | gly | glu | arg | ala | ser | gly | ser | cys |
| NP-5  | val | phe | cys | thr | cys | arg | gly | phe | leu | cys | gly | ser | gly | glu | arg | ala | ser | gly | ser | cys |

|       | 21  | 22  | 23  | 24  | 25  | 26  | 27  | 28  | 29  | 30  | 31  | 32  | 33  | 34  |
|-------|-----|-----|-----|-----|-----|-----|-----|-----|-----|-----|-----|-----|-----|-----|
| NP-1  | arg | ile | arg | gly | arg | ile | his | pro | leu | cys | cys | arg | arg |     |
| NP-2  | arg | ile | arg | gly | arg | ile | his | pro | leu | cys | cys | arg | arg |     |
| NP-3a | arg | val | asn | gly | ala | arg | tyr | val | arg | cys | cys | ser | arg | arg |
| NP-3b | lys | ile | arg | gly | val | arg | phe | pro | phe | cys | cys | pro | arg |     |
| NP-4  | thr | val | asn | gly | val | arg | his | thr | leu | cys | cys | arg | arg |     |
| NP-5  | thr | ile | asn | gly | val | arg | his | thr | leu | cys | cys | arg |     |     |
| HPN-1 | ile | tyr | gln | gly | arg | leu | trp | ala | phe | cys | cys |     |     |     |
| HPN-2 | ile | tyr | gln | gly | arg | leu | trp | ala | phe | cys | cys |     |     |     |
| HPN-3 | ile | tyr | gln | gly | arg | leu | trp | ala | phe | cys | cys |     |     |     |

Antimicrobial Effects of Individual Purified Defensins.

The antimicrobial activity of the individual purified oligopeptides, HNP-1, HNP-2 and HNP-3, was compared to that of the mixture HNP1-3, as shown in Table VI. HNP-1 and HNP-2 were as active as HNP1-3. HNP-3 was less microbicidal than the other oligopeptides against *C. neoformans* C-384, *E. coli* ML-35 and *S. aureus* 502A. The activity of HNP-3 against HSV-1 (McIntyre) and *E. coli* ATCC 29648 was similar to that of HNP-1 and HNP-2.

Immunocytochemistry.

Normal human PMNs that were stained by an immunoperoxidase procedure with antibody to HNP1-3, resulted in a reaction product which was cytoplasmic and granular, suggesting that the HNPs are localized to the cell's granules. Controls performed with preimmune serum or without antiserum showed no peroxidase staining.

It is evident from the above results, that the subject compounds can be used as antimicrobials, having broad range effectiveness against a wide variety of organisms, including viruses, bacteria and fungi. Furthermore, because the subject compounds are naturally occurring, as well as being relatively small oligopeptides, they can be used in a wide variety of applications where long

TABLE II

| | Peptide, % Killing[2] | | | | | |
|---|---|---|---|---|---|---|
| Organism[1] | MCP 1 | MCP 2 | NP 1 | NP 2 | NP 3A | NP 3B |
| 1. *S. albus* | A | B | B | B | D | D |
| 2. *S. aureus* 502A | C | D | D | D | D | D |
| 3. *S. pneumoniae,* Type III | A | | | | | |
| 4. *L. monocytogenes* | A | A | A | A | D | B |
| 5. *E. coli* | C | | B | B | D | C |
| 6. *Ps. aeruginosa* | A | A | A | A | A | A |
| 7. *H. influenzae* | A | A | A | | B | |
| 8. *K. pneumoniae* | A | A | | | A | |
| 9. *S. marscescens* | B | B | | | C | B |
| 10. Streptococcus Group B | | B | | C | | |

[1],[2] Staphylococcus
[3] Streptococcus
[4] Listeria
[5] Escherichia
[6] Pseudomonas
[7] Haemophilus
[8] Klebsiella
[9] Serratia
[2] A >99% killing
B 90–99% killing
C 50–90% killing
D <50% killing

TABLE III

Antibacterial Activity of Rabbit Granulocyte Peptides[a,b]

| ORGANISM | STRAIN/TYPE | NP-1 | NP-2 | NP-3a | NP-3b | NP-4 | NP-5 |
|---|---|---|---|---|---|---|---|
| *Staphylococcus aureus* | 566 | >4.1 | >4.1 | 1.3 | 1.7 | 0.2 | 0.4 |
| *Staphylococcus aureus* | 502A | 2.3 | 2.4 | 0.0 | 0.3 | 0.1 | 0.2 |
| *Staphylococcus aureus* | J.F. | 2.7 | 2.9 | 0.4 | 0.8 | 0.1 | 0.1 |
| *Staphylococcus epidermidis* | UCLA-622 | >4.1 | >4.1 | 1.3 | 1.7 | 0.2 | 0.4 |
| *Streptococcus pneumoniae* | Type III | 3.8 | >3.5 | >3.5 | >3.5 | 4.3 | 1.9 |
| *Streptococcus agalactiae* | Type-I-A | 2.3 | 2.0 | 0.6 | 0.9 | 0.1 | 0.5 |
| *Streptococcus agalactiae* | Type IIIU | 3.9 | 2.9 | 0.3 | 1.2 | 0.2 | 0.4 |
| *Listeria monocytogenes* | 450 | 2.1 | 2.1 | 0.2 | 4.3 | 0.1 | 0.5 |
| *Pseudomonas aeruginosa* | PAO 579 | >4.2 | 3.2 | 3.2 | 4.2 | 0.2 | 0.7 |
| *Escherichia coli* | ATCC 29648 | 1.9 | 0.8 | 0.6 | 1.4 | 0.1 | 0.2 |
| *Klebsiella pneumoniae* | ATCC 13883 | 3.0 | 1.1 | 2.4 | 3.4 | 0.2 | 1.2 |
| *Serratia marcescens* | — | 1.0 | 1.0 | 0.5 | 0.7 | 1.3 | 1.2 |
| *Hemophilus influenzae* | Type 3A | >1.1 | 2.0 | >1.1 | 0.7 | 1.3 | 1.2 |
| *Bordetella bronchiseptica* | UCLA-342 | 0.1 | 0.1 | 0.1 | 0.1 | 0.1 | 0.0 |
| pH 5.8 | | | | | | | |
| *Streptococcus agalactiae* | Type 1A | 0.1 | 0.1 | 0.0 | 0.2 | 0.0 | 0.0 |
| *Listeria monocytogenes* | 450 | 0.2 | 0.1 | 0.0 | 0.0 | 0.0 | 0.1 |
| *Pseudomonas aeruginosa* | PAO 579 | 0.3 | 0.2 | 0.1 | 0.0 | 0.0 | 0.1 |
| *Klebsiella pneumoniae* | ATCC 13883 | 0.6 | 0.5 | 0.4 | 0.2 | 0.3 | 0.1 |
| "High" ionic strength | | | | | | | |
| *Streptococcus agalactiae* | Type 1A | 0.0 | 0.1 | 0.0 | 0.0 | 0.0 | 0.0 |
| *Listeria monocytogenes* | 450 | 0.1 | 0.2 | 0.1 | 0.0 | 0.0 | 0.2 |
| *Pseudomonas aeruginosa* | PAO 579 | 0.1 | 0.0 | 0.1 | 0.0 | 0.0 | 0.0 |
| *Klebsiella pneumoniae* | ATCC 13883 | 0.1 | 0.0 | 0.0 | 0.0 | 0.0 | 0.0 |

Legend for Table III
[a]Bacteria were exposed for 20 min to 50 μg/ml of the indicated purified granulocyte peptide under the standard conditions described in the text.
[b]Bactericidal activity is shown as $\log_{10} N_o/N$, where $N_o$ refers to the initial concentration of CFU/ml (typically $1 \times 10^6$) and N refers to the number of CFU/ml after the 20 min incubation.

TABLE IV

Effects of Substrates on Susceptibility of *S. aureus* to HNP.

| Exp. | Addition | Concentration | Control | +HNP | log₁₀ |
|---|---|---|---|---|---|
| 1 | none | — | $4.9 \times 10^5$ | $5.0 \times 10^5$ | −0.01 |
|  | glucose | 5 mM | $4.9 \times 10^5$ | $2.5 \times 10^3$ | 2.29 |
|  | pyruvate | 5 mM | $1.0 \times 10^5$ | $2.2 \times 10^5$ | −0.34 |
|  | T.S.B. | 1:100 | $1.5 \times 10^6$ | $1.1 \times 10^3$ | 3.13 |
|  | amino ac. | 2.5 mM ea. | $6.5 \times 10^5$ | $5.1 \times 10^5$ | 0.11 |
| 2 | none | — | $1.1 \times 10^6$ | $1.1 \times 10^6$ | 0.00 |
|  | glucose | 5 mM | $8.3 \times 10^5$ | $3.3 \times 10^4$ | 1.40 |
| 3 | none | — | $7.7 \times 10^5$ | $7.7 \times 10^5$ | 0.00 |
|  | glucose | 5 mM | $7.4 \times 10^5$ | $3.2 \times 10^4$ | 1.37 |
|  | T.S.B. | 1:100 | $2.1 \times 10^6$ | $2.5 \times 10^3$ | 2.90 |
|  | TSB + gluc. | 1:100+5 mM | $2.8 \times 10^6$ | $3.8 \times 10^3$ | 2.87 |

The basic incubation medium was 10 mM phosphate buffer, pH 7.4, supplemented with the indicated additions. Incubations were conducted for 2 h at 37° C. with 18 h *S. aureu* cultures grown in T.S.B. (trypticase soy broth). Input concentrations (mean±S.E.M.×10⁶ CFU/ml) were $1.12 \pm 0.17 \times 10^6$ (Exp. 1), $1.52 \pm 0.13 \times 10^6$ (Exp. 2) and $9.3 \pm 0.3 \times 10^5$ (Exp. 3). The mixed amino acids contained alanine, glutamine, histidine, leucine, methionine, and tryptophan (2.5 mM each ). Data show mean CFU/ml after 2 h, and log₁₀ reduction of HNP-treated bacteria relative to control. The sensitizing effect of glucose is established within 20 min (data not shown).

HNP signifies a miixture of human neutrophil peptides (HNP-1; -2; and -3) tested at 50 μg/ml final conc.

TABLE V

Effects of Substrates on Susceptibility of *Pseudomonas aeruginosa* and *Escherichia coli* to HNP.

| Exp. | Addition | Concentration | Control | +HNP | log₁₀ |
|---|---|---|---|---|---|
| *Pseudomonas aeruginosa* PAO 579 | | | | | |
| 1 | none | — | $1.0 \times 10^6$ | $1.1 \times 10^6$ | −0.04 |
|  | glucose | 5 mM | $1.3 \times 10^6$ | $7.7 \times 10^5$ | 0.23 |
|  | T.S.B. | 1:100 | $1.1 \times 10^6$ | $1.7 \times 10^4$ | 1.81 |
|  | TSB + gluc. | 1:100+5 mM | $1.8 \times 10^6$ | $2.3 \times 10^4$ | 1.89 |
| 2 | none | — | $1.2 \times 10^6$ | $1.0 \times 10^6$ | 0.08 |
|  | glucose | 5 mM | $1.1 \times 10^6$ | $7.4 \times 10^5$ | 0.17 |
|  | T.S.B. | 1:100+5 mM | $5.0 \times 10^5$ | $5.5 \times 10^4$ | 0.96 |
| *Escherichia coli* ATCC 29648 | | | | | |
| 3 | none | — | $1.4 \times 10^6$ | $1.2 \times 10^6$ | 0.07 |
|  | glucose | 5 mM | $1.2 \times 10^6$ | $1.3 \times 10^6$ | −0.03 |
|  | T.S.B. | 1:100 | $6.1 \times 10^6$ | $1.4 \times 10^3$ | 3.64 |
|  | pyruvate | 5 mM | $1.5 \times 10^6$ | $1.1 \times 10^6$ | 0.13 |
| 4 | none | — | $1.2 \times 10^6$ | $1.0 \times 10^6$ | 0.08 |
|  | glucose | 5 mM | $1.1 \times 10^6$ | $1.2 \times 10^6$ | −0.04 |
|  | T.S.B. | 1:100 | $6.4 \times 10^6$ | $1.0 \times 10^3$ | 3.81 |
|  | pyruvate | 5 mM | $1.4 \times 10^6$ | $1.2 \times 10^6$ | 0.07 |

The basis incubation medium was 10 mM phosphate buffer, pH 7.4, supplemented with the indicated additions. Incubations were conducted for 2 h at 37° C. with overnight (18 h) cultures of bacteria that has been grown in trypticase soy broth (TSB). The input concentrations (mean±S.E.M.×10⁶ CFU/ml) were as follows: $1.65 \pm 0.1$ (Exp. 1), $1.49 \pm 0.03$ (Exp. 2), $1.48 + 0.02$ (Exp. 3) and $1.25 \pm 0.03$ (Exp. 4). Data shown mean surviving CFU/ml after 2 h incubation and log₁₀ decrease in CFU/ml relative to control incubated without HNP for 2 h.

TABLE VI

Effects of Purified HNP1, 2 and 3 on Test Organisms

| | | Decrease (log₁₀ units) in Concentration of Test Organisms Relative to Input | | | | |
|---|---|---|---|---|---|---|
| EXP. | Log₁₀ INPUT | CONTROL | HNP 1-3 | HNP-1 | HNP-2 | HNP-3 |
| *C. neoformans* C-384 | | | | | | |
| 1 | 6.23 | 0.01 | 3.08 | 3.21 | 3.00 | 1.08 |
| 2 | 6.04 | 0.04 | 1.68 | 2.11 | 1.72 | 0.52 |
| *E. coli* ATCC 29648 | | | | | | |

TABLE VI-continued

Effects of Purified HNP1, 2 and 3 on Test Organisms

| EXP. | Log$_{10}$ INPUT | CONTROL | HNP 1-3 | HNP-1 | HNP-2 | HNP-3 |
|---|---|---|---|---|---|---|
| 1 | 6.15 | −0.79 | 3.52 | 3.22 | 3.43 | 3.61 |
| 2 | 6.23 | −0.79 | 3.55 | 2.04 | 3.60 | 3.47 |
| *E. coli* ML-35 | | | | | | |
| 1 | 6.28 | −0.65 | 2.67 | 2.40 | 2.75 | 0.64 |
| 2 | 6.20 | −0.84 | 1.46 | 1.91 | 1.30 | 0.10 |
| *P. aeruginosa* PAO 579 | | | | | | |
| 1 | 6.24 | 0.31 | 1.16 | 1.20 | 1.39 | 1.07 |
| 2 | 6.45 | 0.22 | 0.47 | 0.64 | 0.91 | 0.35 |
| *S. aureus* 502A | | | | | | |
| 1 | 5.97 | −0.72 | 1.65 | 2.14 | 1.63 | 0.23 |
| 2 | 6.22 | −0.37 | 2.13 | 2.27 | 1.95 | 0.55 |
| HSV-1 (McIntyre) | | | | | | |
| 1 | 6.79 | 0.18 | 2.62 | 2.27 | 2.72 | 2.36 |
| 2 | 6.62 | NT | 2.36 | 2.17 | 1.90 | 2.28 |
| 3 | 6.76 | 0.02 | 1.75 | 1.77 | 1.74 | 1.34 |

Data are shown in log$_{10}$ units. The Input column shows the absolute concentration of bacteria or fungi in CFU/ml or of HSV-1 in PFU/ml at the outset of the incubation. The remaining data show the decrease in CFU/ml, relative to the input, after a 2 hour incubation of fungi or bacteria with 50 μg/ml of a mixture of the three defensins (HNP 1-3) or with 50 μg/ml of the individual peptides. *C. neoformans* was incubated in nutrient-free 10 mM phosphate buffer, pH 7.4, whereas bacteria were incubated in that buffer supplemented with 1% v/v trypticase soy broth. A minus sign indicates that the CFU/ml at 2 h was higher than the input (i.e., that growth had occurred). Experiments with HSC-1 were conducted by exposing the indicated concentration of viruses to 25 μg/ml of HNP1-3 or the individual peptide species for 60 min at 37 C. in Dulbecco's phosphate buffered saline. The HNP1-3 used in this study was reconstituted by mixing the individual purified peptides in a ratio of 1:1:0.5 (HNP-1:HNP-2:HNP-3).

What is claimed is:

1. A method for inhibiting microbial growth in an environment susceptible to said microbial growth, said method comprising:

administering to said environment a microbial growth inhibiting amount of a cationic oligopeptide of not more than about 35 amino acids having a sequence of the formula:

$Z_{0-2}$—($aa^1$)$_a$—($aa^2$)$_b$—cys—$aa^4$—cys—arg—$aa^7$—$aa^8$—$aa^9$—cys—

—$aa^{11}$—$aa^{12}$—$aa^{13}$—glu—arg—$aa^{16}$—$aa^{17}$—gly—$aa^{19}$—cys—

—$aa^{21}$—$aa^{22}$—$aa^{23}$—gly—$aa^{25}$—$aa^{26}$$aa^{27}$—$aa^{28}$—$aa^{29}$—cys—

—cys—($aa^{32}$)$_c$—w

Z is bonded to the terminal amino and may be an acyl group of from one to six carbon atoms having from zero to one amino substituent, alkyl of from one to three carbon atoms or a protective group;

a, b and c are 0 or 1;

the superscripts to the aa which defines amino acid, intends the amino acid number in the polypeptide, except where $aa^9$ intends two amino acids and then all subsequent numbers are increased by one, as well as the numbers in the subsequent definitions;

amino acids 1, 7, 8, 11, 13, 21, 23, 25, 26 and 28 are aliphatic amino acids;

amino acids 2, 4, 9, 12, 16, 17, 19, 22, 27, 29 and 32 are either aliphatic amino acids or aromatic amino acids; and w is the terminal hydroxyl, amino or a peptide of from one to six amino acids having a basic amino acid at the N-terminus.

2. A method according to claim 1, wherein said environment is a formulation for use in vivo.

3. A method according to claim 1, wherein said environment is a protein-containing formulation.

4. A method according to claim 1, wherein $aa^1$ is val or gly;
$aa^2$ is val, ile, arg ser, phe, ala or asp;
$aa^4$ is ala, val, thr or tyr;
$aa^7$ is arg, lys, gly or ile;
$aa^8$ is ala, arg, gln, phe or pro;
$aa^9$ is 2leu, phe, ser or ala;
$aa^{11}$ is leu, pro, ser, gly or ile;
$aa^{12}$ is pro, asn, lys, phe, ser or ala;
$aa^{13}$ is arg, leu, ser or gly;
$aa^{16}$ is arg, phe or ala;
$aa^{17}$ is ala, ser, ile or tyr;
$aa^{19}$ is phe, tyr, asp, ser or thr;
$aa^{21}$ is arg, lys, thr or ile;
$aa^{22}$ is ile, val or tyr;
$aa^{23}$ is arg, asn or gln;
$aa^{25}$ is arg, ala or val;
$aa^{26}$ is ile, leu or arg;
$aa^{27}$ is his, val, phe or trp;
$aa^{28}$ is pro, tyr, ala or thr;
$aa^{29}$ is leu, arg or phe;
$aa^{32}$ is arg, ser, pro or trp; and
w is 0-2 arg.

5. A method according to claim 1, wherein said cationic oligopeptide is of the formula:

$Z'_{0-2}$—val—$aa^2$—cys—$aa^4$—cys—arg—arg—$aa^8$—$aa^9$—cys—
—$aa^{11}$—$aa^{12}$—$aa^{13}$—glu—arg—arg—$aa^{17}$—gly—$aa^{19}$—cys—
—arg—$aa^{22}$—arg—gly—arg—$aa^{26}$—his—$aa^{28}$—leu—cys—
—cys—arg—(arg)$_{0-1}$ wherein:

Z' is methyl, acetyl or an amino acid;
amino acids 2, 4, 8, 9, 11, 17, and 22 are neutral amino acids;
amino acids 12 and 28 are heterocyclic amino acids or neutral amino acids;
amino acid 19 is an aromatic amino acid or hydroxy substituted aliphatic amino acid;
amino acids 13 and 26 are aliphatic amino acids or basic amino acids.

6. A method according to claim 1, wherein said cationic oligopeptide is of the formula:

$Z'_{0-2}$—val—$aa^2$—cys—thr—cys—arg—$aa^7$—phe—$aa^9$—cys—
—gly—$aa^{12}$—gly—glu—arg—ala—$aa^{17}$—gly—$aa^{19}$—cys—
—thr—$aa^{22}$—asn—gly—val—arg—his—$aa^{28}$—leu—cys—
—cys—arg—(arg)$_{0-1}$ wherein:

$aa^2$ and $aa^{12}$ are phe or ser;
$aa^7$ is arg or gly;
$aa^9$ is a hydroxy substituted or unsubstituted aliphatic amino acid;

$aa^{17}$, $aa^{19}$ and $aa^{28}$ are hydroxy substituted amino acids;

$aa^{22}$ is an aliphatic amino acid of from 5 to 6 carbon atoms.

7. A method according to claim 1, wherein said cationic oligopeptide is of the formula:

ala
  —cys—tyr—cys—arg—ile—pro—ala—cys—ile—ala—
asp
    —gly—glu—arg—arg—tyr—gly—thr—cys—ile—tyr—gln—
        —gly—arg—leu—trp—ala—phe—cys—cys, where ala, -, and asp indicate either no amino acid or one of the indicated amino acids.

8. A cationic oligopeptide of the formula:

ala
  —cys—tyr—cys—arg—ile—pro—ala—cys—ile—ala—
asp
    —gly—glu—arg—arg—tyr—gly—thr—cys—ile—tyr—gln—
        —gly—arg—leu—trp—ala—phe—cys—cys where ala, -, and asp indicate either no amino acid or one of the indicated amino acids.

9. In a formulation capable of supporting undesired microbial growth, the improvement which comprises including in said formulation in an amount sufficient to inhibit microbial growth, a cationic oligopeptide according to claim 8.

10. A formulation according to claim 9, having a liquid carrier.

11. A formulation according to claim 9, having a solid carrier.

* * * * *